US012607616B2

(12) United States Patent (10) Patent No.: US 12,607,616 B2

Shiraki et al. (45) Date of Patent: Apr. 21, 2026

(54) DETERMINATION DEVICE, DETERMINATION METHOD, AND SENSOR DEVICE

(71) Applicant: SINTOKOGIO, LTD., Nagoya (JP)

(72) Inventors: Masataka Shiraki, Nagoya (JP); Yoshihisa Suzuki, Nagoya (JP); Masahiko Nagasaka, Nagoya (JP)

(73) Assignee: SINTOKOGIO, LTD., Aichi (JP)

( * ) Notice: Subject to any disclaimer, the term of this patent is extended or adjusted under 35 U.S.C. 154(b) by 310 days.

(21) Appl. No.: 18/474,794

(22) Filed: Sep. 26, 2023

(65) Prior Publication Data

US 2024/0142427 A1 May 2, 2024

(30) Foreign Application Priority Data

Oct. 26, 2022 (JP) ................................. 2022-171744

(51) Int. Cl.
*G01N 33/00* (2006.01)

(52) U.S. Cl.
CPC ..... *G01N 33/0067* (2013.01); *G01N 33/0065* (2013.01)

(58) Field of Classification Search
None
See application file for complete search history.

(56) References Cited

U.S. PATENT DOCUMENTS

| | | | | |
|---|---|---|---|---|
| 10,408,818 B2* | 9/2019 | Bezemer | ................ | A47K 13/24 |
| 11,103,157 B2* | 8/2021 | Gupta | ................... | A61B 5/097 |
| 2013/0110061 A1* | 5/2013 | Abraham | ................ | A61F 13/42 |
| | | | | 604/342 |
| 2015/0257942 A1* | 9/2015 | Kim | ...................... | G08B 25/10 |
| | | | | 604/361 |
| 2015/0301004 A1* | 10/2015 | Carney | .............. | G01N 33/0047 |
| | | | | 73/31.01 |
| 2023/0074448 A1* | 3/2023 | Kanai | ..................... | A61B 5/42 |

FOREIGN PATENT DOCUMENTS

| | | | | | |
|---|---|---|---|---|---|
| JP | 2007167264 A | * | 7/2007 | | |
| JP | 2014-033745 A | | 2/2014 | | |
| JP | 2022104394 A | * | 7/2022 | | |
| KR | 20090119157 A | * | 11/2009 | ............... | A61B 5/01 |
| WO | WO-2021/157108 A | * | 8/2021 | ............. | G06N 20/00 |
| WO | WO-2021/240866 A | * | 12/2021 | ............... | A61B 5/42 |

* cited by examiner

*Primary Examiner* — Daniel S Larkin

(74) *Attorney, Agent, or Firm* — Harness, Dickey & Pierce, P.L.C.

(57) ABSTRACT

In order to provide a novel determination device capable of determining the type of excretion by a subject and a related technology thereof, a determination device includes at least one processor, and the at least one processor carries out a determination process of determining the type of excretion by a subject by referring to a first gas concentration detected by a first gas sensor and a second gas concentration detected by a second gas sensor which differs from the first gas sensor in gas species to be mainly detected.

4 Claims, 3 Drawing Sheets

DETERMINATION DEVICE, DETERMINATION METHOD, AND SENSOR DEVICE

This Nonprovisional application claims priority under U.S.C. § 119 on Patent Application No. 2022-171744 filed in Japan on Oct. 26, 2022, the entire contents of which are hereby incorporated by reference.

TECHNICAL FIELD

The present invention relates to a determination device, a determination method, and a sensor device each of which is for determining a type of excretion.

BACKGROUND ART

In care services or medical services, excretion management for service users is one of important operations.

If automatic detection of excretion of the service users, including automatic detection of a type of the excretion, is possible, a burden of the excretion management on service providers can be significantly reduced.

As a technique for detecting excretion of a service user, for example, the technique disclosed in Patent Literature 1 has been known. The technique disclosed in Patent Literature 1 determines, on the basis of an output signal from an odor sensor and an output signal from a humidity sensor, a type of excreta of a care receiver and whether leakage from a diaper of the care receiver occurs, and then notifies a caregiver of a degree of urgency of treatment for the excretion.

CITATION LIST

Patent Literature

[Patent Literature 1]
Japanese Patent Application Publication, Tokukai, No. 2014-33745

SUMMARY OF INVENTION

Technical Problem

The technique disclosed in Patent Literature 1 is a technique of determining a type of excreta by referring to a combination of a signal from the odor sensor and a signal from the humidity sensor. Unfortunately, in the technique disclosed in Patent Literature 1, used are the odor sensor, the humidity sensor, and a suction fan, and thus a sensor device may have a complicated structure.

An aspect of the present invention is achieved in light of the foregoing problem. It is an object of the aspect of the present invention to provide a novel determination device capable of determining the type of excretion by a subject and a related technology thereof.

Solution to Problem

A determination device in accordance with an aspect of the present invention includes at least one processor, the at least one processor being configured to carry out a determination process of determining a type of excretion by a subject by referring to a first gas concentration detected by a first gas sensor and a second gas concentration detected by a second gas sensor differing from the first gas sensor in gas species to be mainly detected.

A determination method in accordance with an aspect of the present invention includes: an acquisition process of at least one processor acquiring a first gas concentration detected by a first gas sensor and a second gas concentration detected by a second gas sensor differing from the first gas sensor in gas species to be mainly detected; and a determination process of the at least one processor determining a type of excretion by a subject by referring to the first gas concentration and the second gas concentration.

A sensor device in accordance with an aspect of the present invention includes a first gas sensor; and a second gas sensor differing from the first gas sensor in gas species to be mainly detected, the sensor device being configured to transmit, to a determination device configured to determine a type of excretion by a subject, a first gas concentration detected by the first gas sensor and a second gas concentration detected by the second gas sensor.

Advantageous Effects of Invention

An aspect of the present invention makes it possible to provide a novel determination device capable of determining a type of excretion by a subject and a related technology thereof.

DESCRIPTION OF EMBODIMENTS (Configuration of Determination System)

Figure 1:
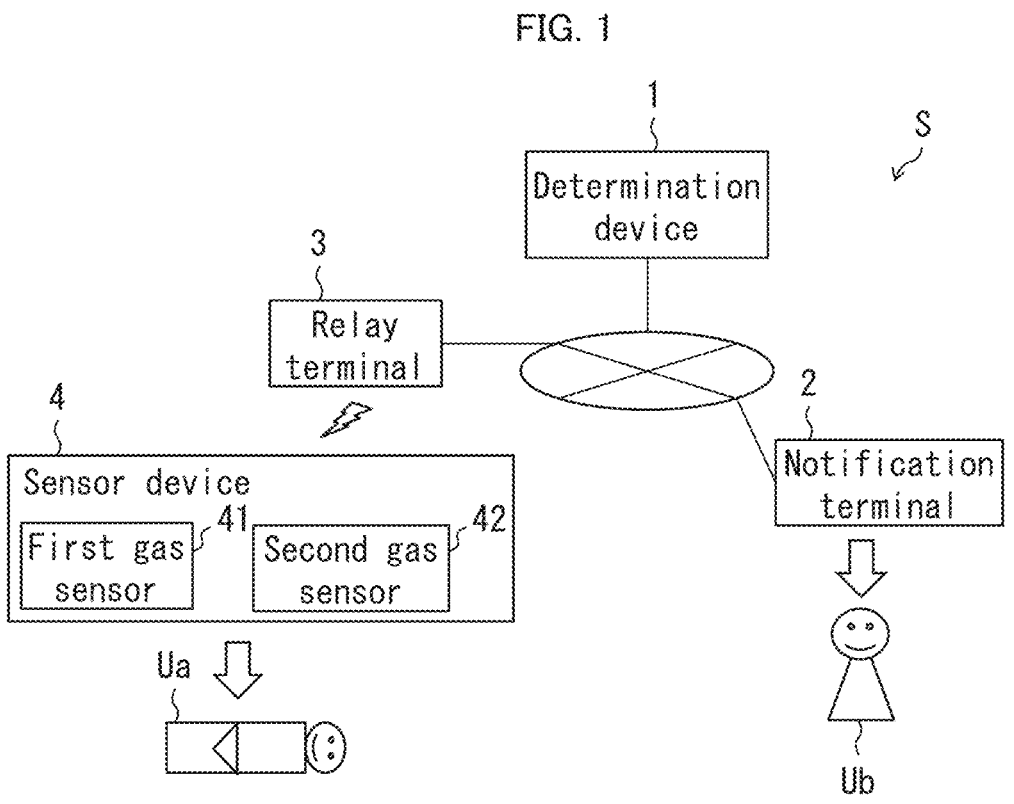
FIG. 1 is a view schematically illustrating a configuration of a determination system in accordance with an embodiment of the present invention.

With reference to FIG. 1, the following will describe a determination system S in accordance with an embodiment of the present invention. FIG. 1 is a view schematically illustrating a configuration of the determination system S in accordance with an embodiment of the present invention.

The determination system S is a system configured to, in facilities for providing care services and/or medical services, determine a type of excretion by a service user Ua who is a subject and notify a service provider Ub of a result of the determination. In the present embodiment, the type of the excretion is determined to be either one of a stool or flatus. Note that, in the present specification, the "flatus" means a phenomenon in which a gas is discharged from a body without defecation. The "flatus" does not include a phenomenon in which a gas is discharged from a body during defecation, a phenomenon in which a gas is discharged from a stool after defecation, and a phenomenon in which a gas is discharged from urine after urination.

As illustrated in FIG. 1, the determination system S includes a determination device 1, a notification terminal 2, a relay terminal 3, and a sensor device 4. The determination device 1 and the notification terminal 2 communicate with each other via a network. The determination device 1 and the relay terminal 3 communicate with each other via a network. The relay terminal 3 and the sensor device 4 communicate with each other without using any network (communicate with each other via, for example, near field wireless communication).

The sensor device 4 is attached to the service user Ua. As an example, the sensor device 4 is attached to the inside of underwear (diaper, underpants, panties, or the like) of the service user Ua. The sensor device 4 includes a first gas sensor 41 and a second gas sensor 42 and is configured to transmit, to the determination device 1, an output signal from the first gas sensor 41 and an output signal from the second gas sensor 42, via the relay terminal 3. The sensor device 4 further includes a processor and a communication interface, and the processor performs communication from the sensor device 4 to the relay terminal 3 with use of the communication interface.

The first gas sensor 41 is configured to selectively detect a first gas that belongs to a predetermined gas species. The second gas sensor 42 is configured to selectively detect a second gas that belongs to a predetermined gas species differing from the gas species to which the first gas belongs. That is, the second gas sensor differs from the first gas sensor in gas species to be mainly detected. In other words, a detection-target gas species of the second gas sensor differs from that of the first gas sensor. Hereinafter, in the present specification, a simple term "gas sensor(s)" means both of or either one of the first gas sensor 41 and the second gas sensor 42.

An output signal from the first gas sensor includes information indicating a time series of a first gas concentration, and an output signal from the second gas sensor includes information indicating a time series of a second gas concentration. Hereinafter, for simple descriptions, the information indicating a time series of a first gas concentration and the information indicating a time series of a second gas concentration are simply referred to as "first gas concentration" and "second gas concentration", respectively.

In the present embodiment, the first gas is derived from a stool and is, for example, hydrogen sulfide. That is, the first gas sensor 41 is a hydrogen sulfide sensor. In addition, in the present embodiment, the second gas is derived from flatus and is, for example, hydrogen. That is, the second gas sensor 42 is a hydrogen sensor.

Figure 2:
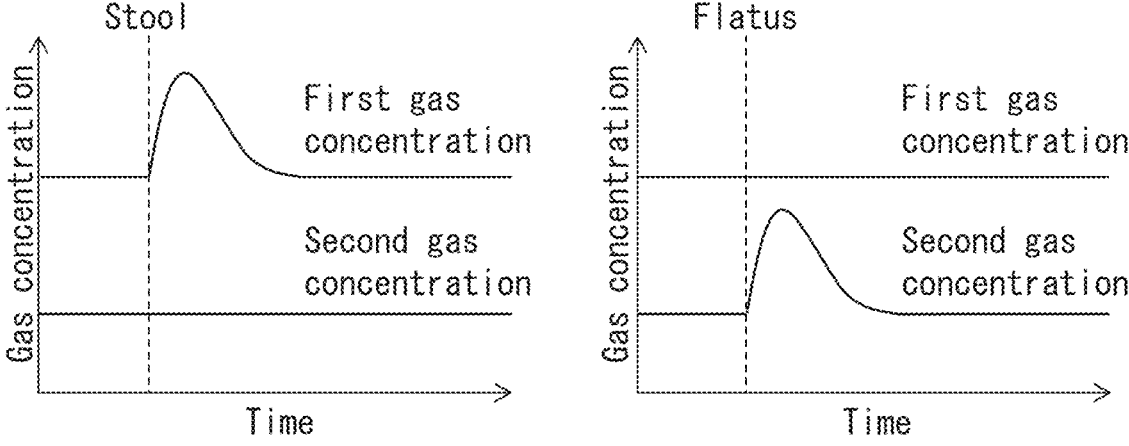
FIG. 2 is a graph schematically illustrating changes in first gas concentration and second gas concentration respectively corresponding to gas derived from a stool and gas derived from flatus, in the embodiment of the present invention.

Note that, for simplification, the following descriptions are made on the assumption that gas derived from a stool contains the first gas and does not contain the second gas, and gas derived from flatus contains the second gas and does not contain the first gas. In this case, in a case where the excretion by the service user Ua is a stool, the first gas concentration and the second gas concentration change as indicated in a left graph shown in FIG. 2. In a case where the excretion by the service user Ua is flatus, the first gas concentration and the second gas concentration change as indicated in a right graph shown in FIG. 2.

The relay terminal 3 is disposed in the vicinity of the sensor device 4. As an example, the relay terminal 3 is disposed in a room in which the service user Ua is present. The relay terminal 3 receives, from the sensor device 4, an output signal(s) from a gas sensor(s). Further, the relay terminal 3 transmits, to the determination device 1, the output signal(s) from the gas sensor(s) received from the sensor device 4. In the present embodiment, as the relay terminal 3, a smartphone is used. Alternatively, a stationary wireless relay device may be used as the relay terminal 3.

The determination device 1 is disposed outside the facility as described above. As an example, the determination device 1 is disposed in a data center. The determination device 1 receives, from the relay terminal 3, the output signal(s) from the gas sensor(s). Further, the determination device 1 determines a type of excretion by the service user Ua with reference to the output signal(s) from the gas sensor(s) received from the relay terminal 3. The determination device 1 then transmits a notification screen including a result of the determination to the notification terminal 2. Note that, for example, a computer disposed in the facility may be alternatively used as the determination device 1.

The notification terminal 2 is carried by the service provider Ub. The notification terminal 2 receives, from determination device 1, data indicating the notification screen. In addition, the notification terminal 2 includes a display of a touch panel type and is configured to display the notification screen on the display on the basis of the data received from the determination device 1. In the present embodiment, as the notification terminal 2, a smartphone is used. Note that, in the following descriptions, transmitting data indicating a notification screen is described as transmitting the notification screen, and receiving data indicating each screen is described as receiving the screen.

(Configuration of Determination Device)

Figures 3, 4:
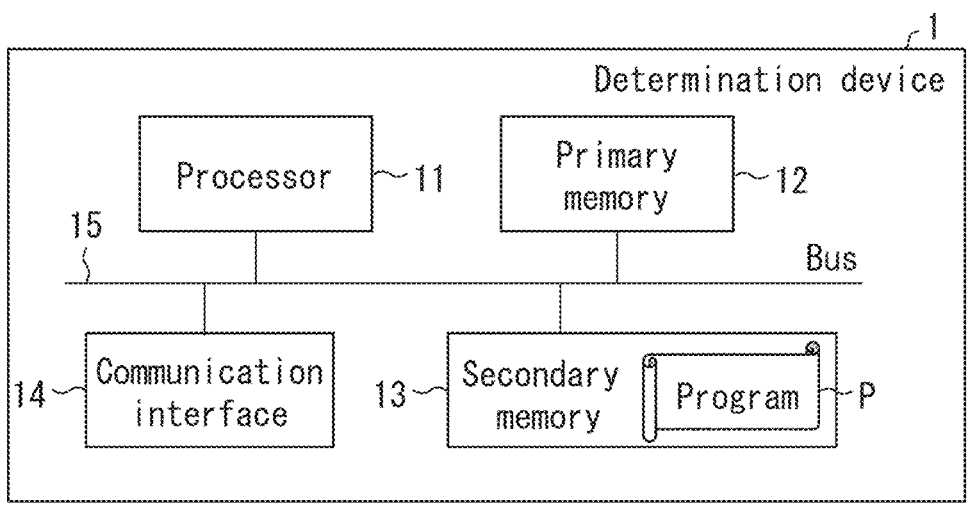
FIG. 3 is a block diagram illustrating a configuration of a determination device included in the determination system illustrated in FIG. 1.
FIG. 4 is a flowchart showing a flow of a determination method carried out by the determination device illustrated in FIG. 3.

With reference to FIG. 3, the following will describe the configuration of the determination device 1 included in the determination system S. FIG. 3 is a block diagram showing the configuration of the determination device 1 included in the determination system S illustrated in FIG. 1.

As illustrated in FIG. 3, the determination device 1 includes a processor 11, a primary memory 12, a secondary memory 13, a communication interface 14, and a bus 15. The processor 11, the primary memory 12, the secondary memory 13, and the communication interface 14 are connected with each other via the bus 15. Examples of a device usable as the determination device 1 include a workstation constituting a cloud server.

The secondary memory 13 stores a determination program P. The processor 11 loads, on the primary memory 12, the determination program P stored in the secondary memory 13. The processor 11 then carries out processes included in a determination method M1 (described later) in accordance with instructions included in the determination program P loaded on the primary memory 12. Examples of a device usable as the processor 11 include a central processing unit (CPU). Examples of a device usable as the primary memory 12 include a semiconductor random access memory (RAM). Examples of a device usable as the secondary memory 13 include a hard disk drive (HDD).

The communication interface 14 is an interface for communicating with the notification terminal 2 and the relay terminal 3 via a network. Examples of an interface usable as the communication interface 14 include an Ethernet (registered trademark) interface. Examples of a usable network include a personal area network (PAN), a local area network (LAN), a campus area network (CAN), a metropolitan area network (MAN), a wide area network (WAN), a global area network (GAN), and an internetwork containing a combination thereof. The internetwork may be an intranet, or may be an extranet, or may be the Internet.

Note that the determination program P for causing the processor 11 to carry out the determination method M1 may be stored in a computer-readable non-transitory tangible storage medium. This storage medium can be the secondary memory 13 or another storage medium. For example, a tape, a disk, a card, a semiconductor memory, a programmable logic circuit, or the like can be used as said another storage medium.

The present embodiment employs a configuration in which a single processor (the processor 11) is used to carry out the determination method M1. Note, however, that the present invention is not limited to this. That is, alternatively, employed may be a configuration in which a plurality of processors are used to carry out the determination method M1. In this case, the plurality of processors for carrying out the determination method M1 may be provided in a single computer and be configured to be communicable with each other via a bus or may be dispersedly provided in a respective plurality of computers and be configured to be communicable with each other via a network. For example, the following alternative aspects are also possible: an aspect in which processors included in a respective plurality of computers constituting a cloud server work together to carry out the determination method M1; and an aspect in which the processor 11 of the determination device 1 and a processor of the notification terminal 2 work together to carry out the determination method M1.

(Flow of Determination Method)

Figure 5:
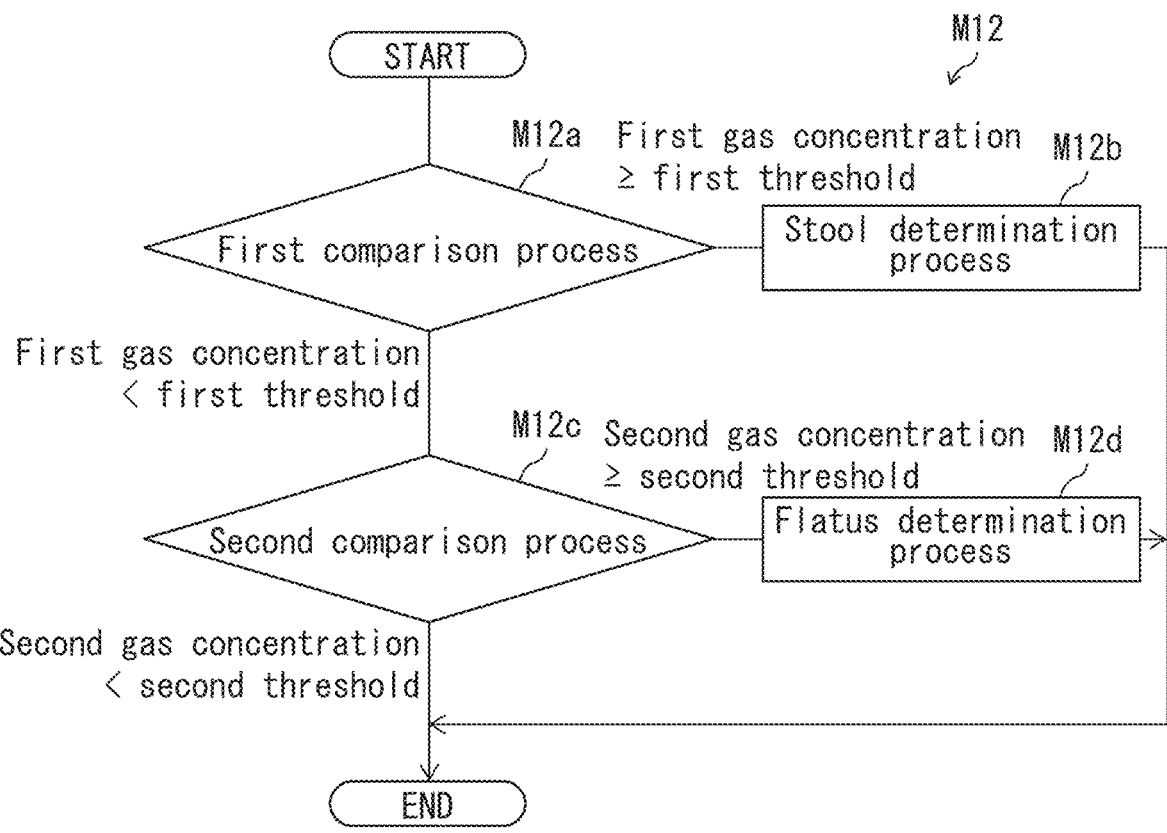
FIG. 5 is a flowchart showing a specific example of a determination process included in the determination process shown in FIG. 4.

With reference to FIGS. 4 and 5, the following will describe a flow of the determination method M1 carried out by the determination device 1.

FIG. 4 is a flowchart showing a flow of the determination method M1 carried out by the determination device 1 illustrated in FIG. 3. As illustrated in FIG. 4, the determination method M1 includes an acquisition process M11, a determination process M12, and a notification process M13. In the present embodiment, the acquisition process M11, the determination process M12, and the notification process M13 are carried out by the processor 11 of the determination device 1.

The acquisition process M11 is a process of acquiring a first gas concentration (hydrogen sulfide gas concentration) detected by the first gas sensor 41 and a second gas concentration (hydrogen gas concentration) detected by the second gas sensor 42. In the present embodiment, the processor 11 acquires, from the sensor device 4, a gas concentration(s) detected by a gas sensor(s) via the communication interface of the sensor device 4 and the communication interface 14 of the determination device 1. However, the present invention is not limited to such a configuration. As an example, the processor 11 may acquire the first gas concentration and the second gas concentration by reading, from the secondary memory 13, the first gas concentration and the second gas concentration that are stored in the secondary memory 13.

The determination process M12 is a process of determining a type of excretion by the service user Ua by referring to the first gas concentration and the second gas concentration. A specific example of the determination process M12 will be described later with reference to another drawing.

Note that, the processor 11 may subject the gas concentrations acquired in the acquisition process M11 to preprocessing and carry out the determination process M12 with use of the gas concentrations subjected to the preprocessing. Examples of such preprocessing include: a scaling process, such as normalization and standardization; a filtering process, such as high-pass filtering and low-pass filtering; and an interpolation process, such as linear interpolation and spline interpolation.

The notification process M13 is a process of notifying the notification terminal 2 used by the service provider Ub of the type of excretion determined in the determination process M12. In the present embodiment, the processor 11 transmits a notification screen indicating the type of excretion determined, to the notification terminal 2 with use of the communication interface 14.

(Specific Example of Determination Process)

With reference to FIG. 5, the following will describe a specific example of the determination process M12. FIG. 5 is a flowchart showing a specific example of the determination process M12 included in the determination method M1 shown in FIG. 4.

The determination process M12 can be constituted by, for example, a first comparison process M12a, a stool determination process M12b, a second comparison process M12c, and a flatus determination process M12d, as shown in FIG. 5. In the present embodiment, the first comparison process M12a, the stool determination process M12b, the second comparison process M12c, and the flatus determination process M12d are carried out by the processor 11 of the determination device 1.

The first comparison process M12a is a process of comparing the first gas concentration with a predetermined first threshold.

In a case where, in the first comparison process M12a, the first gas concentration has been determined to be greater than or equal to the first threshold, the stool determination process M12b is carried out. The stool determination process M12b is a process of determining that a type of excretion by the service user Ua is a stool. The determination process is caused to end after a stool determination is made.

In a case where, in the first comparison process M12a, the first gas concentration has been determined to be less than the first threshold, the second comparison process M12c is carried out. The second comparison process M12c is a process of comparing the second gas concentration with a predetermined second threshold.

In a case where, in the second comparison process M12c, the second gas concentration has been determined to be greater than or equal to the second threshold, the flatus determination process M12d is carried out. The flatus determination process M12d is a process of determining that a type of excretion by the service user Ua is flatus. The determination process is caused to end after a stool determination is made.

Effect of the Present Embodiment

As described above, the determination device 1 in accordance with the present embodiment includes the at least one processor 11, the at least one processor 11 being configured to carry out the determination process M12 of determining a type of excretion by the subject Ua by referring to the first gas concentration detected by the first gas sensor 41 and the second gas concentration detected by the second gas sensor 42 differing from the first gas sensor 41 in gas species to be mainly detected.

According to such a configuration, the processor 11 refers to selectively detected gas concentrations of two or more gas species different from each other. Thus, it is possible to achieve a device that enables determination of a type of excretion by the subject Ua.

Further, in the present embodiment, the first gas sensor 41 is configured to mainly detect a first gas derived from a stool, and the second gas sensor 42 is configured to mainly detect a second gas that is derived from flatus and that differs from the first gas.

According to such a configuration, the processor 11 refers to the first gas concentration which is a concentration of gas derived from a stool and the second gas concentration which is a concentration of gas derived from flatus. Thus, it is possible to achieve a technique that enables an accurate determination as to whether the excretion by the subject Ua is a stool or flatus.

Further, in the present embodiment, in the determination process M12, (i) in a case where the first gas concentration detected by the first gas sensor 41 is greater than or equal to a first threshold, the processor 11 determines that the type of the excretion by the subject Ua is a stool. Further, in the determination process M12, (ii) in a case where the first gas concentration detected by the first gas sensor 41 is less than the first threshold, and the second gas concentration detected by the second gas sensor 42 is greater than or equal to a second threshold, the processor 11 determines that the type of excretion by the subject Ua is flatus.

According to such a configuration, only in a case where, on the basis of the first gas concentration, it is confirmed that a type of excretion is not a stool, whether or not the type of excretion is flatus is determined on the basis of the second gas concentration. Thus, it is possible to reduce the possibility that, in spite of the fact that a type of excretion is a stool, the type of excretion is erroneously determined to be flatus. Therefore, it is possible to reduce the possibility that the erroneous determination delays a treatment for the stool of the service user.

Further, in the present embodiment, the processor 11 is configured to further carry out the notification process M13 of notifying the notification terminal 2 used by the service provider Ub of the type of excretion determined.

According to such a configuration, the service provider Ub is notified of a result of the determination. Thus, it is possible to achieve a device that enables reduction in a burden of excretion management for the subject Ua on the service provider Ub.

Further, the determination method M1 in accordance with the present embodiment includes: the acquisition process M11 of the at least one processor 11 acquiring a first gas concentration detected by the first gas sensor 41 and a second gas concentration detected by the second gas sensor 42 differing from the first gas sensor 41 in gas species to be mainly detected; and the determination process M12 of the at least one processor 11 determining a type of excretion by a subject Ua by referring to the first gas concentration and the second gas concentration.

According to such a configuration, the processor 11 refers to selectively detected gas concentrations of two or more gas species different from each other. Thus, it is possible to achieve a method that enables determination of a type of excretion by the subject Ua.

Further, the sensor device 4 in accordance with the present embodiment includes the first gas sensor 41 and the second gas sensor 42 differing from the first gas sensor 41 in gas species to be mainly detected, and the sensor device 4 is configured to transmit, to the determination device 1 configured to determine a type of excretion by a subject Ua, a first gas concentration detected by the first gas sensor 41 and a second gas concentration detected by the second gas sensor 42.

According to such a configuration, it is possible to achieve the sensor device 4 usable for determining a type of excretion by the subject Ua. The sensor device 4 includes the first gas sensor 41 and the second gas sensor 42, both of which are gas sensors, and thus has a simple configuration, compared with a sensor device of a conventional technique constituted by a combination of a gas sensor and a humidity sensor.

VARIATION

In the present embodiment, an aspect in which the determination method M1 is carried out by the determination device 1 is described, but the present invention is not limited to this. That is, the determination method M1 may be carried out by the sensor device 4, or may be carried out by the relay terminal 3, or may be carried out by the notification terminal 2.

In a case where the sensor device 4 carries out the determination method M1, the sensor device 4 transmits, to the relay terminal 3, a determination result that the sensor device 4 itself has been obtained, and then the relay terminal 3 transmits, to the determination device 1, the determination result obtained from the sensor device 4. In a case where the relay terminal 3 carries out the determination method M1, the sensor device 4 transmits, to the relay terminal 3, an output signal(s) from a gas sensor(s), and then the relay terminal 3 transmits, to the determination device 1, a determination result that the relay terminal 3 itself has obtained. In either case, the determination device 1 does not carry out the determination method M1 and functions as a notification device for transmitting, to the notification terminal 2, a notification screen indicating a determination result obtained from the relay terminal 3.

In a case where the notification terminal 2 carries out the determination method M1, the sensor device 4 transmits, to the relay terminal 3, an output signal(s) from a gas sensor(s), and then the relay terminal 3 transmits, to the determination device 1, the output signal(s) obtained from the sensor device 4. The determination device 1 does not carry out the determination method M1 and functions as a relay device for transmitting, to the notification terminal 2, the output signal(s) obtained from the relay terminal 3. In this case, the notification terminal 2 displays a notification screen including a determination result that the notification terminal 2 itself has obtained.

In the present embodiment, an aspect in which a type of excretion is determined to be either one of a stool or flatus is described, but the present invention is not limited to this. The type of excretion to be determined may be any combination of two or more types of excretion. Examples of such types of excretion to be determined include a stool, urine, and flatus. The determination of the type of excretion may be carried out such that a distinction of the stool is made between a bloody stool and a stool other than the bloody stool. Similarly, the determination of the type of excretion may be carried out such that a distinction of the urine is made between bloody urine and urine other than the bloody urine. In a case where the number of the types of excretion to be determined is three or more, a configuration may be employed in which the sensor device 4 includes as many gas sensors as the types of excretion to be determined, the gas sensors being configured to selectively detect corresponding gasses that are derived from excretion to be determined and that belong to gas species different from each other, and the processor 11 refers to all the gas concentrations detected. Alternatively, another configuration may be employed in which the sensor device 4 includes the first gas sensor 41 and the second gas sensor 42, and the processor 11 refers to two gas concentrations detected and determines the three or more types of excretion on the basis of a predetermined algorithm.

In the present embodiment, an aspect in which the first gas sensor 41 detects a hydrogen sulfide gas, and the second gas sensor 42 detects a hydrogen gas is described, but the present invention is not limited to this. For example, the first gas sensor 41 may be configured to selectively detect, as a first gas derived from a stool, gas derived from a stool other than hydrogen sulfide. The second gas sensor 42 may be configured to selectively detect, as a second gas derived from flatus, gas derived from flatus other than hydrogen. In addition, the sensor device 4 may further include a third gas sensor, and the third gas sensor may be configured to selectively detect, as a third gas derived from urine, gas containing iron.

Note that, flatus contains methane gas, carbon dioxide gas, and nitrogen gas as well as the hydrogen gas. Thus, (i) a configuration may be employed in which the methane gas is used as the second gas, and a methane sensor is used as the second gas sensor 42, (ii) a configuration may be employed in which the carbon dioxide gas is used as the second gas, and a carbon dioxide sensor is used as the second gas sensor 42, or (iii) a configuration may be employed in which the nitrogen gas is used as the second gas, and a nitrogen sensor is used as the second gas sensor 42.

Among the hydrogen gas, the methane gas, the carbon dioxide gas, and the nitrogen gas, the hydrogen gas is contained in flatus in the highest concentration. Further, the hydrogen gas is contained in an atmospheric air in a lower concentration. Thus, the hydrogen gas is presumably the most suitable gas for the second gas derived from flatus. However, hydrogen has a small molecular weight and thus is likely to penetrate underwear of the service user Ua and disperse into an atmospheric air. Thus, a hydrogen gas concentration may decrease in a short time inside the underwear in which the second gas sensor 42 is present. In a case where such decrease in hydrogen gas concentration in a short time interferes with determination of a type of excretion, one possible option is to use, as the second gas, the methane gas, the carbon dioxide gas, or the nitrogen gas. Among these, the methane gas is suitable as the second gas derived from flatus, since the methane gas is contained in an atmospheric air in a lower concentration than the nitrogen gas and the carbon dioxide gas.

In the present invention, an algorithm for determining a type of excretion in the determination process M12 is not limited to the algorithm described above for the present embodiment. Examples of such an algorithm for determining a type of excretion include: an algorithm in which used is a learned model subjected to machine learning with use of training data in which a type of excretion to be determined, a first gas concentration, and a second gas concentration are associated with each other; and an algorithm in which an actual value is used as a reference for comparison, wherein the actual value has been set on the basis of a correspondence between a type of each past excretion by a subject and a combination of a first gas concentration and a second gas concentration that have been detected in the past excretion.

In addition, in the present invention, response characteristics of the first gas sensor 41 and the second gas sensor 42 with respect to excretion by a subject are not limited to the response characteristics described above for the present embodiment. For example, the first gas sensor 41 may be sensitive more to the first gas than to the second gas and also be sensitive to the second gas. The same applies to the second gas sensor 42.

SUPPLEMENTARY NOTE

The present invention is not limited to the embodiments above, but can be altered by a skilled person in the art within the scope of the claims. The present disclosure also encompasses, in its technical scope, any embodiment derived by combining technical means disclosed in differing embodiments as appropriate.

The invention claimed is:

1. A determination device comprising at least one processor, the at least one processor being configured to carry out a determination process of determining a type of excretion by a subject by referring to a first gas concentration detected by a first gas sensor and a second gas concentration detected by a second gas sensor, the first gas sensor being configured to detect a first gas derived from a stool, the second gas sensor being configured to detect a second gas that is derived from flatus and that differs from the first gas, in the determination process, (i) in a case where the first gas concentration detected by the first gas sensor is greater than or equal to a first threshold, the at least one processor determining that the type of excretion by the subject is a stool and thereafter ending the determination process, and in the determination process, (ii) in a case where the first gas concentration detected by the first gas sensor is less than the first threshold, and the second gas concentration detected by the second gas sensor is greater than or equal to a second threshold, the at least one processor determining that the type of excretion by the subject is flatus.

2. The determination device according to claim 1, wherein the at least one processor is configured to further carry out a notification process of notifying a notification terminal used by a service provider of the type of excretion determined.

3. A determination method comprising:

an acquisition process of at least one processor acquiring a first gas concentration detected by a first gas sensor and a second gas concentration detected by a second gas sensor; and a determination process of the at least one processor determining a type of excretion by a subject by referring to the first gas concentration and the second gas concentration, the first gas sensor being configured to detect a first gas derived from a stool, the second gas sensor being configured to detect a second gas that is derived from flatus and that differs from the first gas, and in the determination process, the at least one processor determining that the type of excretion by the subject in the following manner:

(i) in a case where the first gas concentration detected by the first gas sensor is greater than or equal to a first threshold, the at least one processor determines that the type of excretion is a stool and thereafter ends the determination process; and (ii) in a case where first gas concentration detected by the first gas sensor is less than the first threshold, and the second gas concentration detected by the second gas sensor is greater than or equal to a second threshold, the at least one processor determines that the type of excretion is flatus.

4. A sensor device comprising:

a first gas sensor configured to detect a first gas derived from a stool; and a second gas sensor configured to detect a second gas that is derived from flatus and that differs from the first gas, the sensor device being configured to transmit, to a determination device configured to determine a type of excretion by a subject, a first gas concentration detected by the first gas sensor and a second gas concentration detected by the second gas sensor, in the determination device, at least one processor carrying out a determination process of determining the type of excretion by the subject by referring to the first gas concentration detected by the first gas sensor and the second gas concentration detected by the second gas sensor; and in the determination process, (i) in a case where the first gas concentration detected by the first gas sensor is greater than or equal to a first threshold, the at least one processor determining that the type of excretion by the subject is a stool and thereafter ending the determination process;

(ii) in a case where the first gas concentration detected by the first gas sensor is less than the first threshold, and the second gas concentration detected by the second gas sensor is greater than or equal to a second threshold, the at least one processor determining that the type of excretion by the subject is flatus.

* * * * *